(12) United States Patent
Alchemy et al.

(10) Patent No.: US 11,848,109 B1
(45) Date of Patent: Dec. 19, 2023

(54) SYSTEM AND METHOD OF DETERMINING FINANCIAL LOSS FOR WORKER'S COMPENSATION INJURY CLAIMS

(71) Applicant: Alchemy Logic Systems Inc., Santa Rosa, CA (US)

(72) Inventors: John William Alchemy, Santa Rosa, CA (US); Jerry Lee Artz, St. Paul, MN (US); Roger Bastow, Wichita, KS (US)

(73) Assignee: Alchemy Logic Systems, Inc., Santa Rosa, CA (US)

( * ) Notice: Subject to any disclaimer, the term of this patent is extended or adjusted under 35 U.S.C. 154(b) by 366 days.

(21) Appl. No.: 16/939,960

(22) Filed: Jul. 27, 2020

Related U.S. Application Data

(60) Provisional application No. 62/879,904, filed on Jul. 29, 2019.

(51) Int. Cl.
  *G16H 50/70* (2018.01)
  *G16H 10/60* (2018.01)
  *G16H 70/20* (2018.01)
  *G06Q 10/10* (2023.01)
  *G06Q 40/08* (2012.01)

(52) U.S. Cl.
  CPC ............. *G16H 50/70* (2018.01); *G06Q 10/10* (2013.01); *G06Q 40/08* (2013.01); *G16H 10/60* (2018.01); *G16H 70/20* (2018.01)

(58) Field of Classification Search
  CPC ........ G06Q 10/10; G06Q 40/08; G16H 10/60; G16H 15/00
  See application file for complete search history.

(56) References Cited

U.S. PATENT DOCUMENTS

| 4,916,611 A | 4/1990 | Doyle, Jr. et al. |
| 4,987,538 A | 1/1991 | Johnson et al. |
| 5,182,705 A | 1/1993 | Barr et al. |

(Continued)

FOREIGN PATENT DOCUMENTS

| CA | 2707207 A1 | 6/2009 |
| WO | WO2008006117 A2 | 1/2008 |
| WO | WO2018224937 A1 | 12/2018 |

OTHER PUBLICATIONS

Ammendolia C, Cassidy D, Steensta I, et al. Designing a workplace return-to-work program for occupational low back pain: an intervention mapping approach. BMC Musculoskelet Disord. 2009;10:65. Published Jun. 9, 2009. doi:10.1186/1471-2474-10-65 (Year: 2009).*

(Continued)

*Primary Examiner* — Joseph D Burgess
(74) *Attorney, Agent, or Firm* — Haverstock & Owens a Law Corporation

(57) ABSTRACT

A system and method is implemented to provide a construction of three separate timelines for comparison and analysis including a query to a historical accurate database. One or more data sets are compared to a high accuracy database that contains reviewed and accurate historical impairment data. An analysis of the historical data can facilitate the output of a temporary impairment rating, apportionment, future care demand of resources and one or more recommendations for the most effective manner to achieve MMI. The collection of outputs are used to create an injury map nexus.

19 Claims, 4 Drawing Sheets

(56) References Cited

U.S. PATENT DOCUMENTS

| | | | |
|---|---|---|---|
| 5,367,675 A | 11/1994 | Cheng et al. |
| 5,517,405 A | 5/1996 | McAndrew et al. |
| 5,544,044 A | 8/1996 | Leatherman |
| 5,613,072 A | 3/1997 | Hammond |
| 5,778,345 A | 7/1998 | McCartney |
| 5,911,132 A | 6/1999 | Sloane |
| 6,003,007 A | 12/1999 | DiRienzo |
| 6,065,000 A | 5/2000 | Jensen |
| 6,604,080 B1 | 8/2003 | Kern |
| 6,810,391 B1 | 10/2004 | Birkhoelzer et al. |
| 6,865,581 B1 | 3/2005 | Cloninger, Jr. |
| 6,954,730 B2 | 10/2005 | Lau et al. |
| 6,957,227 B2 | 10/2005 | Fogel |
| 7,337,121 B1* | 2/2008 | Beinat .................... G16H 50/50 705/3 |
| 7,401,056 B2 | 7/2008 | Kam |
| 7,440,904 B2 | 10/2008 | Hasan et al. |
| 7,475,020 B2 | 1/2009 | Hasan et al. |
| 7,509,264 B2 | 3/2009 | Hasan et al. |
| 7,630,911 B2 | 12/2009 | Kay |
| 7,707,046 B2 | 4/2010 | Kay |
| 7,707,047 B2 | 4/2010 | Hasan et al. |
| 7,778,849 B1 | 8/2010 | Hutton |
| 7,813,944 B1 | 10/2010 | Luk |
| 7,870,011 B2 | 1/2011 | Kay |
| 7,904,309 B2 | 3/2011 | Malone |
| 7,930,190 B1 | 4/2011 | Milanovich |
| 7,949,550 B2 | 5/2011 | Kay |
| 7,970,865 B2 | 6/2011 | DeCesare et al. |
| 8,019,624 B2 | 9/2011 | Malone |
| 8,041,585 B1 | 10/2011 | Binns et al. |
| 8,065,163 B2 | 11/2011 | Morita et al. |
| 8,069,066 B2 | 11/2011 | Stevens et al. |
| 8,185,410 B2 | 5/2012 | Brigham |
| 8,301,575 B2 | 10/2012 | Bonnet et al. |
| 8,346,573 B2 | 1/2013 | Glimp et al. |
| 8,489,413 B1 | 7/2013 | Larson et al. |
| 8,489,424 B2 | 7/2013 | Tasan et al. |
| 8,510,134 B1 | 8/2013 | Sweat et al. |
| 8,527,303 B2 | 9/2013 | Kay |
| 8,615,409 B1 | 12/2013 | McKown |
| 8,630,878 B1 | 1/2014 | Kravets et al. |
| 8,725,524 B2 | 5/2014 | Fano |
| 8,725,538 B2 | 5/2014 | Kay |
| 8,751,252 B2 | 6/2014 | Chamberlain |
| 8,751,263 B1 | 6/2014 | Cave et al. |
| 8,751,266 B2 | 6/2014 | Stang |
| 8,775,216 B1 | 7/2014 | Amick et al. |
| 8,864,663 B1 | 10/2014 | Kahn et al. |
| 8,868,768 B2 | 10/2014 | Sokoryansky |
| 8,888,697 B2 | 11/2014 | Bowman et al. |
| 8,900,141 B2 | 12/2014 | Smith et al. |
| 8,910,278 B2 | 12/2014 | Davne et al. |
| 8,930,225 B2 | 1/2015 | Morris |
| 8,959,027 B2 | 1/2015 | Kusens |
| 8,954,339 B2 | 2/2015 | Schaffer |
| 9,002,719 B2 | 4/2015 | Tofte |
| 9,015,055 B2 | 4/2015 | Tirinato et al. |
| 9,020,828 B2 | 4/2015 | Heidenreich |
| 9,229,917 B2 | 1/2016 | Larcheveque |
| 9,710,600 B1 | 7/2017 | Dunleavy |
| 2001/0027331 A1 | 10/2001 | Thompson |
| 2001/0044735 A1 | 11/2001 | Colburn |
| 2001/0053984 A1 | 12/2001 | Joyce |
| 2002/0069089 A1 | 6/2002 | Larkin |
| 2002/0077849 A1 | 6/2002 | Baruch |
| 2004/0044546 A1 | 3/2004 | Moore |
| 2005/0060184 A1 | 3/2005 | Wahlbin |
| 2005/0177403 A1 | 8/2005 | Johnson |
| 2005/0256744 A1 | 11/2005 | Rhode |
| 2006/0161456 A1 | 7/2006 | Baker |
| 2006/0287879 A1 | 12/2006 | Malon |
| 2007/0118406 A1 | 5/2007 | Killin |
| 2007/0250352 A1 | 10/2007 | Tawil |
| 2008/0046297 A1 | 2/2008 | Shafer |
| 2008/0133297 A1 | 6/2008 | Schmotzer |
| 2008/0154672 A1* | 6/2008 | Skedsvold ..... G06Q 10/063114 705/7.26 |
| 2008/0183497 A1 | 7/2008 | Soon-Shiong |
| 2009/0099875 A1 | 4/2009 | Koenig |
| 2010/0042435 A1 | 2/2010 | Kay |
| 2010/0106520 A1 | 4/2010 | Kay |
| 2010/0106526 A1 | 4/2010 | Kay |
| 2010/0114609 A1 | 5/2010 | Duffy, Jr. et al. |
| 2010/0217624 A1 | 8/2010 | Kay |
| 2010/0240963 A1* | 9/2010 | Brigham ................ G06Q 40/08 600/300 |
| 2011/0077980 A1 | 3/2011 | Kay |
| 2011/0077981 A1 | 3/2011 | Kay |
| 2011/0145012 A1 | 6/2011 | Nightingale |
| 2011/0161115 A1 | 6/2011 | Hampton |
| 2011/0257919 A1 | 10/2011 | Reiner |
| 2011/0257993 A1 | 10/2011 | Shahani |
| 2011/0313785 A1 | 12/2011 | Lash |
| 2011/0313912 A1 | 12/2011 | Teutsch |
| 2012/0022884 A1 | 1/2012 | Chillemi |
| 2012/0102026 A1 | 4/2012 | Fortune |
| 2012/0130751 A1 | 5/2012 | McHugh |
| 2012/0232924 A1 | 9/2012 | Bingham |
| 2012/0245973 A1 | 9/2012 | Pandya |
| 2012/0278095 A1 | 11/2012 | Homchowdhury |
| 2012/0284052 A1 | 11/2012 | Saukas |
| 2013/0024214 A1 | 1/2013 | Schoen et al. |
| 2013/0132122 A1 | 5/2013 | Walsh |
| 2014/0052465 A1 | 2/2014 | Madan |
| 2014/0058763 A1 | 2/2014 | Zizzamia |
| 2014/0073486 A1 | 3/2014 | Ahmed |
| 2014/0136216 A1 | 5/2014 | Beebe |
| 2014/0172439 A1 | 6/2014 | Conway et al. |
| 2014/0201213 A1 | 7/2014 | Jackson |
| 2014/0249850 A1 | 9/2014 | Woodson |
| 2014/0278479 A1 | 9/2014 | Wang et al. |
| 2014/0278830 A1 | 9/2014 | Gagne |
| 2014/0303993 A1 | 10/2014 | Florian |
| 2015/0019234 A1 | 1/2015 | Cooper |
| 2015/0221057 A1 | 8/2015 | Raheja et al. |
| 2015/0235334 A1 | 8/2015 | Wang et al. |
| 2015/0242585 A1 | 8/2015 | Spiegel |
| 2015/0278462 A1 | 10/2015 | Smoley |
| 2015/0286792 A1 | 10/2015 | Gardner |
| 2015/0324523 A1 | 11/2015 | Parthasarathy et al. |
| 2016/0063197 A1 | 3/2016 | Kumetz |
| 2016/0125544 A1 | 5/2016 | Edwards |
| 2016/0283676 A1 | 9/2016 | Lyon |
| 2016/0292371 A1 | 10/2016 | Alhimiri |
| 2017/0140489 A1 | 5/2017 | Ziobro |
| 2017/0154374 A1 | 6/2017 | Iglesias |
| 2017/0177810 A1 | 6/2017 | Fulton |
| 2017/0228517 A1 | 8/2017 | Saliman |
| 2017/0255754 A1 | 9/2017 | Allen |
| 2017/0316424 A1 | 11/2017 | Messana |
| 2017/0352105 A1 | 12/2017 | Billings |
| 2018/0025334 A1 | 1/2018 | Pourfallah |
| 2018/0279919 A1 | 10/2018 | Bansbach |
| 2019/0065686 A1 | 2/2019 | Crane |
| 2020/0126645 A1 | 4/2020 | Robbins |
| 2020/0279622 A1 | 9/2020 | Heywood |
| 2020/0286600 A1 | 9/2020 | De Brouwer |

OTHER PUBLICATIONS

Programming languages. (2004). In W. S. Bainbridge (Ed)., Berkshire encyclopedia of human-computer interaction. Berkshire Publishing Group. Credo Reference: https://search.credoreference.com/content/entry/berkencyhci/programming_languages/0? institutionid=743 (Year: 2004), 5 pages.

Rondinelli, Robert D., Guides to the Evaluation of Permanent Impairment, 2008 Sixth Edition, American Medical Association.

American College of Occupational and Environmental Medicine, Occupational Medicine Practice Guidelines, 2004, Second Edition, OEM Press, Beverly Farms, MA.

CA Medical Treatment Utilization Schedule, Proposed Chronic Pain Medical Treatment Guidelines, Jun. 2008, 83 pages.

(56) References Cited

OTHER PUBLICATIONS

In B. Pfaffenberger, Webster's new World Computer Dictionary (10th ed), Houghton Mifflin Harcourt, Credo reference: https://search.credoreference.com/content/entry/webster.com/database (year 2003).

Hakkinen, Arja, et al. "Muscle strength, pain, and disease activity explain individual subdimensions of the Health Assessment Questionaire disability index, especially in women with rheumatoid arthritis." Annals of the rheumatic diseases 65.1 (2006): 30-34. (Year: 2006).

"CA DWC Releases 4th Edition of Physician's Guide to Medical Practice in CA WC", Apr. 5, 2016, workcompwire.com, 7 pages.

State of California Department of Industrial Relations Division of Workers' Compensation, Physician's Guide to Medical Practice in the California Workers' Compensation System, Fourth Edition, 2016, 137 pages.

Cocchiarella, Linda and Andersson, Gunnar B. J., Guides to the Evaluation of Permanent Impairment, 2001, Fifth Edition, American Medical Association, 618 pages.

Park, Y., Butler, R.J. (2000), Permanant Partial Disability Awards and Wage Loss, Journal of Risk and Insurance, 67(3), 331, Retrieved from https"//dialog.proquest.com/professional/docview/769439662, Year 2000, 18 pages.

"Physician's Guide to Medical Practice in the California Workers Compensation System", 2016, State of California Department of Industrial Relations Division of Workers Compensation, 4th ed., all pages. (Year 2016).

Wasiak, Radoslaw, et al. "Measuring Return To Work." Journal of Occupational Rehabilitation 17.4 (2007): 766-781. (Year: 2007). 16 pages.

\* cited by examiner

SYSTEM AND METHOD OF DETERMINING FINANCIAL LOSS FOR WORKER'S COMPENSATION INJURY CLAIMS

RELATED APPLICATIONS

This Patent Application claims priority under 35 U.S.C. 119(e) of the U.S. provisional patent application, Application No. 62/879,904, filed on Jul. 29, 2019, and entitled "METHOD TO DETERMINE TIMELINE AND FINANCIAL LOSS FOR WORKERS' COMPENSATION INJURY CLAIMS," which is hereby incorporated in its entirety by reference.

FIELD OF THE INVENTION

The present invention is generally directed to telemedicine. More specifically, the present invention is directed to a system and method of addressing the communication breakdown due to a lack of understanding of the overall context of the medical case management strategy which can delay effective and timely case management and accurate case closure.

BACKGROUND OF THE INVENTION

A poor understanding of worker's compensation claim contextual data such as treatment failure results, order of treatment sequence and an adjacent influence of such actions can all result in failure of case closure in the existing worker's compensation process. This can also affect work flows and transparency in the worker's compensation process and related medical-legal sectors. Additionally, lack of insight into a compensation claim's current status, delays in treatment and the costs associated with such delays can result in monetary loss to stakeholders, decreased well being for the patient and a delayed return to work.

The current approach to the treatment of work injuries and the management of injury claims is inconsistent across different medical systems and individual providers. Insights into the obstacles and losses associated with the claims are not readily available or easily understood. This can include embedded services of third party vendors with inefficient systems that introduce further delay and confusion in the execution of medical treatment and events such a physical therapy schedule and a delivery of a durable good. The result is a lack of organization that is widespread and unnecessary administrative costs to employers, insurance carriers and medical providers. This all creates a potential negative impact on the patient's well being and ultimately a higher cost to society.

SUMMARY OF THE INVENTION

The present invention is directed to a system and method of producing an injury map of an injury claim and management efficiency analysis including medical direction and decision making support. The system and method addresses the circumstances where treatment milestones provide a construction of three separate timelines for comparison and analysis including a query to a historical accurate database. One or more data sets are compared to a high accuracy database that contains reviewed and accurate historical impairment data. An analysis of the historical data can facilitate the output of a temporary impairment rating, apportionment, future care demand of resources and one or more recommendations for the most effective manner to achieve Maximum Medical Improvement (MMI). The collection of outputs are used to create an injury map nexus.

In a first aspect, a system for optimizing an injury map and treatment actions for a worker's compensation claim across three separate timelines comprises a worker date of injury, a date of doctor's first report for the injury and a date of injury review, wherein each of the worker date of injury, the date of doctor's first report and the date of injury review are associated with a single worker's compensation claim and grouped according to a cohort, which is an experimental database of similar matched injury severities, also known as a historical accurate database (HAD), for the injury and a server configured to receive the worker date of injury, the date of doctor's first report and the date of injury review, generate an ideal injury timeline based on the worker date of injury, a timeline based on the date of doctor's first report and a timeline based on the date of injury review, wherein each of the timelines are based on the cohort for the injury and output the ideal injury timeline for the worker date of injury, the timeline for the date of doctor's first report and the timeline for the date of injury review to one or more stakeholder's for the injury. In some embodiments, each of the timelines comprises an apportionment of injury liability, a whole person impairment rating, a maximum medical improvement date, cost metrics for the injury and injury treatment status. In some of these embodiments, the injury treatment status for the injury comprises one or more of completed and pending treatments, treatments behind and on schedule and treatment days delayed. In some embodiments, the cost metrics for the injury comprise one or more of days of delay, medical financial loss and total monetary loss. In some embodiments, the ideal injury timeline based on the worker date of injury, the timeline based on the date of doctor's first report and the timeline based on the date of injury review are generated according to average historical data for the cohort stored at the server. In some embodiments, the historical data for the cohort is updated at the server for each new injury. In further embodiments, the date of doctor's first report and the date of injury review are assigned a delta value based on the date of injury. In some embodiments, the ideal injury timeline based on the worker date of injury, the timeline based on the date of doctor's first report and the timeline based on the date of injury review are comparable across a single provider's office, a single medical group, a single claim adjuster, a single insurance company and a single employer. In further embodiments, the ideal injury timeline based on the worker date of injury, the timeline based on the date of doctor's first report and the timeline based on the date of injury review are comparable across geographic locations.

In another aspect, a method of producing one or more injury maps for a worker's compensation injury claim comprises receiving at a client device one or more injury inputs comprising one or more of a worker date of injury, a date of doctor's first report for the injury, and a date of injury review, grouping the injury claim into an injury cohort, at a server, based on the injury cohort generating an ideal injury timeline for the worker date of injury, a timeline for the date of doctor's first report and a timeline for the date of injury review; and outputting one or more of the ideal injury timeline for the worker date of injury, the timeline for the date of doctor's first report and the timeline for the date of injury review to one or more stakeholder's for the injury. In some embodiments, each of the timelines comprises an apportionment of injury liability, a whole person impairment rating, a maximum medical improvement date, cost metrics for the injury and injury treatment status. In some of these embodiments, the injury treatment status for the injury comprises one or more of completed and pending treatments, treatments behind and on schedule and treatment days delayed. In some embodiments, the cost metrics for the injury comprise one or more of days of delay, medical financial loss and total monetary loss. In some embodiments, the ideal injury timeline based on the worker date of injury, the timeline based on the date of doctor's first report and the timeline based on the date of injury review are generated according to average historical data for the cohort stored at the server. In some embodiments, the historical data for the cohort is updated at the server for each new injury. In further embodiments, the date of doctor's first report and the date of injury review are assigned a delta value based on the date of injury. In some embodiments, the ideal injury timeline based on the worker date of injury, the timeline based on the date of doctor's first report and the timeline based on the date of injury review are comparable across a single provider's office, a single medical group, a single claim adjuster, a single insurance company and a single employer. In further embodiments, the ideal injury timeline based on the worker date of injury, the timeline based on the date of doctor's first report and the timeline based on the date of injury review are comparable across geographic locations.

In a further aspect, a system for calculating a delta value of treatment for a worker's compensation claim comprises a worker date of injury, a date of doctor's first report for the injury, wherein the date of doctor's first report comprises the true beginning of the worker's compensation claim, wherein the worker date of injury and the date of doctor's first report are associated with a single worker's compensation claim and grouped according to a cohort for the injury and a server for receiving the worker date of injury and the date of doctor's first report and wherein the based on a comparison of a treatment timeline for worker date of injury and a treatment timeline for the date of doctor's first report, the server outputs a delta value of care for the worker. In some embodiments, the delta value of care is expressed in one of three conditions, negative, neutral and positive.

DETAILED DESCRIPTION OF THE EMBODIMENTS

Figure 1:
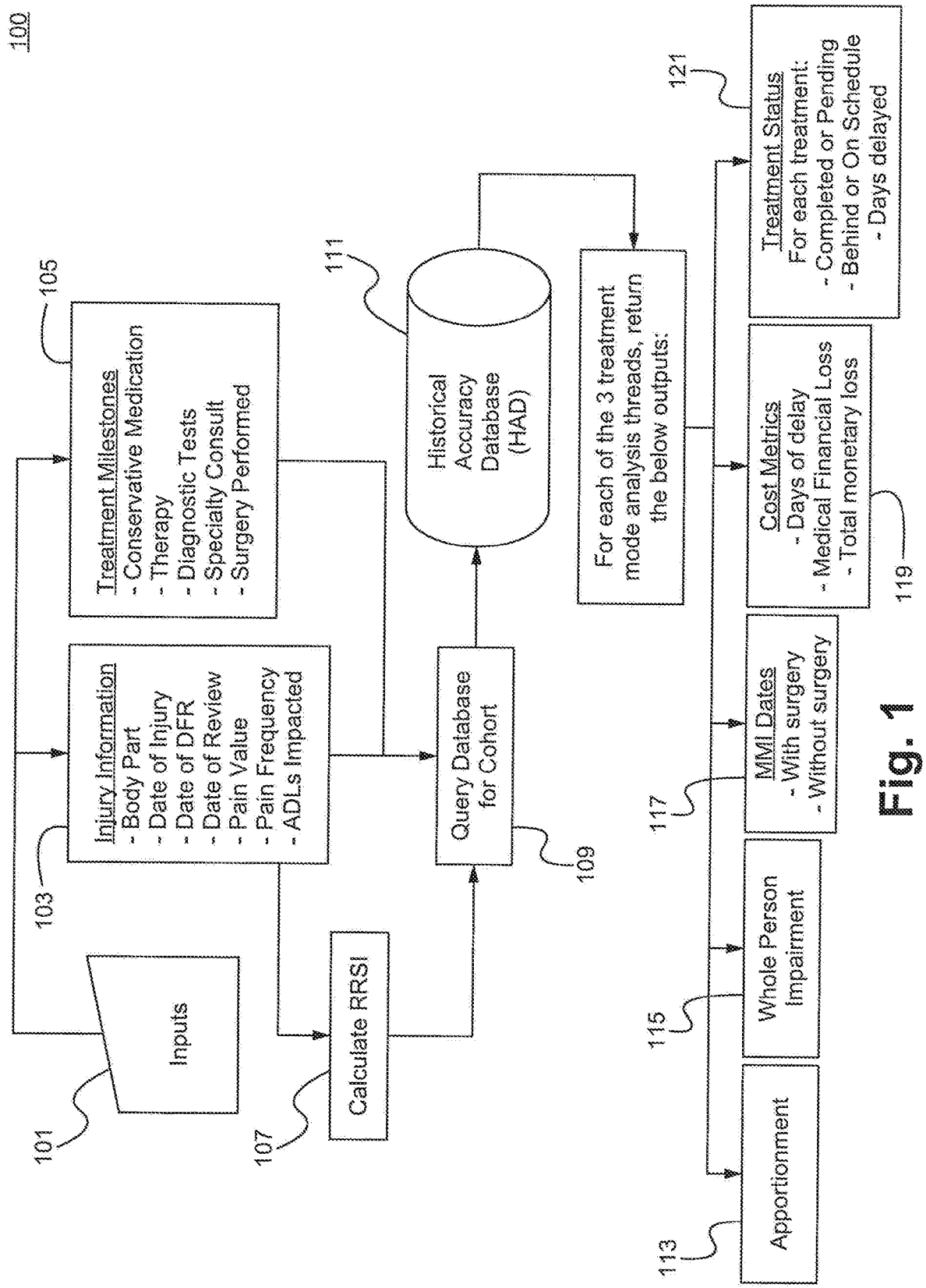
FIG. 1 illustrates a flow chart illustrating an injury map nexus comprising three distinct treatment analysis threads, in accordance with some embodiments

The present invention is directed to a system and method of producing an injury map of an injury claim and management efficiency analysis including medical direction and decision making support. The system and method addresses the circumstances where treatment milestones provide a construction of three separate timelines for comparison and analysis including a query to a historical accurate database. One or more data sets are compared to a high accuracy database that contains reviewed and accurate historical impairment data. An analysis of the historical data can facilitate the output of a temporary impairment rating, apportionment, future care demand of resources and one or more recommendations for the most effective manner to achieve MMI. The collection of outputs are used to create an injury map nexus.

Reference will now be made in detail to implementations of a system and method of a system and method of determining financial loss for worker's compensation injury claims. The same reference indicators will be used throughout the drawings and the following detailed description to refer to the same or like parts. In the interest of clarity, not all of the routine features of the implementations described herein are shown and described. It will be appreciated that in the development of any such actual implementation, numerous implementation-specific decisions can be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The present invention produces an injury map for an injury claim. The injury map includes timelines, next steps, urgency levels and other claim data. The results of the map benefit all stakeholders and allows the claim to proceed in a timely and organized predictable manner. Particularly, by generating and outputting the injury map for the claim, the claim is identifiable and can be accessed at a central location, creating increased efficiency, a more reliable and optimized worker's claim process. Specifically, all of the injury map claim data can be created and stored in an accessible, centralized and secure location such that each stakeholder is able to access and see each level and step of the worker's claim process beyond which was earlier possible. The injury map is a tool that standardizes the delivery of care and allows comparisons of various stakeholder effectiveness including Medical Provider Networks (MPNs), insurance carriers, medical providers, legal service and litigation impact, geographic location, and regional and state level legislation.

The MMI date and the insights within the injury map are fact driven and systematic. The injury map allows stakeholders to objectively identify MMI using impairment measurement scalars identified by an Administrative Rule Set (ARS), such as the American Medical Association's (AMA's) 5$^{th}$ Edition. Permanent impairment is the basis for a permanent disability calculation and ultimately claim settlement.

Further applications and methods may be applied to the data set at any point in the injury map to create continuous improvements and centralize and optimize the calculations for settlement costs, apportionments, functional work status, remaining active treatment costs, and any necessary care beyond MMI. The injury map also tracks data integrity as the claim progresses so that there can be confidence in the underlying data.

Data integrity had two fundamental components 1) data completeness and 2) data quality. Data completeness is discussed in the U.S. patent application Ser. No. 16/124,960 to Alchemy et al. (the '960 Application), and entitled "Method of and System for Providing a Confidence Measurement Rating Process," filed Sep. 7, 2018, which is hereby incorporated by reference, where data completeness is a value of the total expected data inputs according to the ARS. Data quality is the level of reporting compliance present in the report with the instructions provided by the ARS. For example, the AMA's 5$^{th}$ Edition requires upper extremity range of motion measurements to be 1) reported to the nearest degree of finding with an actual goniometer and requires b) a minimum of two trial measurements, two measurements that are consistent if they fall within 10% of each other and c) opposite side measurements to serve as a baseline for impairment calculations.

For example, an injured right shoulder range of motion data entry of the highest integrity (100%) would involve the right injured shoulder moving in six planes of motion, with two trials on each place (12 total measurements) to the nearest degree (e.g. flexion 166, 171) and a complete similar data set for the left uninjured side (12 total measurements) for a total of 24 independent measurements divided between the right injured shoulder and the left uninjured shoulder.

To determine a data integrity score of an example data set, the data completeness is multiplied by the data quality. For example, only 6 of the 24 required measurements have been completed (25% data completeness) and the data quality is a D or 63% (where Grade A+ is 100% and Grade F is 59%) then the data integrity score for the data set is 0.25*0.63=0.16 (16%). The data integrity for the data set can then be compared to similar data sets stored within a high accuracy database (HAD). For example, the data set for a Recovery Score Index (RSI) such as discussed within U.S. patent application Ser. No. 15/833,541 (the '541 Application), and entitled "Method to Determine Highly Accurate Objective Maximum Medical Improvement (MMI) Status and Dating Assignment," filed Dec. 6, 2017, which hereby incorporated by reference, can be compared with similar RSI scores to determine whether the RSI score fits within a desired normal value. Particularly, the data sets for each specific claim can be compared to data sets for similar injuries to determine a reference of standard of deviation (SD) from a mean value. Additionally, each data set and the integrity score for the data set can be accessible to the stakeholders to in a centralized, secure and reliable location. This enables each stakeholder to access and determine an integrity score for their data and a comparison to the data sets for similar injuries in a fast efficient manner not previously possible.

Collectively, the grouping of these data results comprises the "injury map nexus." The injury map nexus provides transparency and insight for all stakeholders to determine the immediate next treatment action and date of action to achieve MMI for the worker's compensation injury. This also enables the stakeholders to calculate the financial costs for the compensation claim to the date and as it relates to the treatment offerings. The injury map nexus optimizes stakeholder resources, saving time and money for the industry. Additionally, the injury map nexus allows stakeholders to understand and determine the non-obvious time delays throughout the system. For example, it can be determined with the injury map nexus that a particular vendor has a sub-optimal delivery system as reflected by a delay in bringing a patient to therapy, imaging or a specialty consultation. Conversely, the stakeholders can identify the high performing vendors in the system according to improved or shortened delivery times.

The injury map can be referenced using the HAD, such as described above. The comparison facilitates a query to similarly matched body parts to be adjusted for severity using the RSL. Particularly, as claim data is continuously uploaded during claim progression, the query to the HAD can be adjusted to represent the most recent condition of the claim. This allows stakeholders to determine the specific claim status and costs and compare against similar claims to project further costs, system efficiency, settlement apportionment and future care projections.

The injury map reflects a customized digitization of an individual's worker's injury for injury management, understanding and directives within the worker's compensation system. The digital injury map creates a holistic retrospective review of claim costs, efficiency and deficiency, and medical time management. The injury map also creates and guides prospective claim instructions and transparency within a sometimes obfuscated multiple delivery system resulting in a variable understanding and execution of best medical practices that reduces financial losses for the stakeholders. All told, the injury map provides insight into the "claim resource leakage" which are the invisible costs of money and time.

The injury map nexus comprises three treatment analysis threads and is dependent on three key date inputs 1) date of injury (DOI), 2) date of first report (DFR) and 3) date of review (DOR). DOI is the date of actual injury and/or the date of the administratively recognized injury. The DFR is the date that the individual is seen by a medical provider and formal medical attention is provided. For example, this can be the date of a first emergency room visit, urgent care visit or visit to an outpatient clinic. The third nexus date DOR, is the date which provides the reference in time for the retrospective, the present and the prospective query and recommendations. This is also the date that anchors the associated analysis of the system mode of delivery efficiencies and recommendations. Ultimately, the DOR creates the infrastructure used to determine the delays in case management and loss incurred to the stakeholders.

Following an input of the DOI, the DFR and the DOR, data queries are requested for the presence and absence of treatment (e.g. medications, therapy, etc.), diagnostic testing (e.g. x-ray, MRI studies, etc.) and specialty consulting with or without intervention procedures (surgery, medication, etc.). The query is populated with data from the clinical data set and the injury map generates and outputs a summary of completed and incomplete actions necessary to advance the claim to MMI. The actions can be those that were required, but not performed and those that will be required and performed in the future. In some embodiments, the summary of completed and incomplete actions are stored within a secured centralized database accessible to the stakeholders. The summary of completed and incomplete actions can be sent automatically to each stakeholder such that each stakeholder is aware of their role and liabilities within the worker's compensation claim.

FIG. 1 illustrates a flow chart 100 illustrating an injury map nexus comprising three distinct treatment analysis threads, in accordance with some embodiments and such as described above. As shown within FIG. 1, injury inputs for the injured worker are entered in the step 101. In some embodiments, the injury inputs are entered using a website or application that enables a user to enter one or more inputs at a user or client terminal. In some embodiments, the client terminal comprises one or more computer systems such as desktop computers, laptop computers, network computers, handheld data storage devices, wireless communication devices, cellular telephones, etc. The injury inputs 101 can comprise injury information 103 such as an identification of an injured body part, the DOI, DFR, and DOR, such as described above, pain value, pain frequency and activities of daily living (ADLs) that are impacted. The injury inputs 101 can also comprise actions performed to date or the treatment milestones 105, such as medication prescriptions and the date of prescription, therapies prescribed and the date, diagnostic tests and the date and any specialty consultations and date, including any surgeries performed and the date. Based on the worker's injury a RSI can be calculated 107 and the injury grouped according to a cohort for the injury 109. The injury, including the DOI, the DFR and the DOR can then be compared to similar injuries using the HAD 111, such as described above. Based on the DOI, the DFR and the DOR an ideal injury timeline for each of the three treatment modes and analysis can be output. As shown within FIG. 1, in some embodiments, each of the timelines comprises an apportionment of injury liability 113, a whole person impairment rating 115, a maximum medical improvement date 117, cost metrics for the injury 119 and injury treatment status 121.

In some embodiments, one or more coordinating rule sets (CRSs) are used to configure the underlying care delivery expectation times and tolerance of time delivery. The one or more CRSs are comprised of two underlying practice standards and/or mandates 1) best medical practices (BMPs) and 2) best administrative practices (BAPs).

BMPs can be an example of evidence based medical guidelines derived from scientific studies and present available research. For example, a shoulder strain injury can require a trial of conservative care to include anti-inflammatory medications and physical therapy prior to a MRI scan to eliminate internal derangement. Similarly, a MRI scan many be necessary prior to specialty consulting because the consultant will need this information prior to a surgical intervention determination. Examples of BMPs include the California Worker's Compensation Medical Treatment Utilization Schedule (MTUS) or the Official Disability Guidelines (ODG).

BAPs can be statutory or jurisdictional in origin. For example, MTUS in the recommendations of treatment ordering and authorization. The MTUS is a collection of state mandated treatment guidelines that may have elements of BMPs, however, because it is incorporated into the labor code law, the MTUS is also a BAP. California worker's compensation requires an authorization determination to be approved or denied within 5 business days after service to an insurance carrier. Thus, in some embodiments, such requirements can be incorporated within the rules sets of the injury map.

Treatment for an injury can be linear in treatment progression or non-linear. In some embodiments, the injury map employs non-linear variable mapping logic, which allows reconfigurable thread logic commands. A linear claim has a defined chain of treatment expectation. A cumulative trauma injury such as an ankle strain is an example. In a linear claim the one or more CRSs configure care in the following order of demand with regards to BMP and BAP: 1) anti-inflammatory medication trial for two weeks, 2) therapy trial, 3) diagnostic imaging (x-ray, MRI, etc.), 4) specialty consultation, 5) possible surgery and rehabilitation. In contrast, a non-linear injury may have a fragmented chain of treatment. A badly displaced ankle from a fall can be an example. For the non-linear injury, the ordering of timeline care delivery expectation must be re-ordered. For example, 1) an injury is seen in the emergency room, 2) an x-ray is performed, 3) an orthopedic consultant is called, 4) surgery is performed, 5) medications are prescribed (all on the same date). However, therapy is not indicated until 6 weeks after surgery. The non-linear variable mapping logic allows a flexible reconfiguration of the DFR and the DOR as the circumstance of treatment dictate. The non-linear variable mapping logic creates increased utility due in scope and application because of its ability to adapt to multiple clinical scenarios, not only linear cases.

The DOI, as described above is the optimal timeline anchored to the actual date of injury as recognized by the one or more stakeholders. The DOI timeline is the master reference that guides and predicts the expectations for treatment, imaging, consultation and procedures for the claim. The DOI timeline is used to determine any variance of the actual claim management and also to detect any delays in the delivery of care and services to the injured worker.

The DFR timeline is the actual beginning of the worker's compensation claim and treatment as the one or more stakeholders become aware of the claim and the worker becomes eligible for care. The DFR timeline serves as the variable to which the DOI timeline is referenced. Based on a comparison of the DOI timeline and the DFR timeline, a variance or delta value of care can be calculated. The delta value is expressed in three conditions a) negative delta value, for example −5 days, indicates that the delivery of care and/or services has occurred earlier than as expected according to the DOI, b) a neutral delta value, for example 0 days, indicates that the delivery of care has occurred consistent with the DOI timeline and c) a positive value, for example +5 days indicates that the deliver of care has occurred later than expected according to the DOI timeline.

Additionally, such as described above, and described within U.S. patent application Ser. No. 14/996,067 (the '067 Application), and entitled "Methods of Obtaining High Accuracy Impairment Ratings and to Assist Data Integrity in the Impairment Rating Process," filed Jan. 14, 2016, which is hereby incorporated by reference contains a database of similarly classified body part injuries or injury cohorts. The HAD comprises the DOR and provides the reference in time for the retrospective, the present and the prospective care, such as described above. The timelines of care or services for the injury cohorts can be compared to the DFR, to calculate a delta value to compare the claim care and delivery of services and also to determine delays in case management and stakeholder financial losses. This comparison is unique because it allows a direct comparison of multiple different care environments and claim efficiency across one or more provider's office, one or more medical groups, one or more claim adjusters and one or more employers that may offer injury care in multiple geographic locations. Additionally, for each new client the injury cohort data can be updated and centrally stored within the HAD creating a larger central database and greater efficiency as the amount of claims and relevant data increases. This thread also creates a comparison of the timelines to detect the best mode of delivery of care. For example, insurance company A may show a data trend indicating +21 days delay (delta) bringing patients to therapy and insurance company B shows a +5 days delay (delta). Further investigation may then show that insurance company B has a better logistics vendor and a better integrated infrastructure network than company A. This creates an analytical tool that can track trends in behavior, effectiveness and claim length across multiple variables.

The summation of the three different analysis threads, such as described above can be used to create the injury map nexus or report card. The report card comprises the summary of the above results and can also include and impairment rating and MMI determination, such as described within the '541 Application. The report card comprises a snapshot of claim vital signs that can be generated and outputted to the one or more stakeholders. In some embodiments, the report card can comprise MMI status and/or anticipated MMI, recovery status, claim severity, estimate of whole person impairment (% WPI), apportionment of liability and pre-existing conditions, estimate of claim settlement value, administrative financial loss (expenses from delays in claim management), work status (RSI driven), completed treatment, pending treatment actions (present and future). The report card can be generated and shared to the one or more stakeholders to alert the stakeholders to delays in care, pending and future care milestones and to provide an insight into continuous claim data trends. It is the ability to provide an insight into claim data trends that allows additional benefits to the present invention, which are not otherwise obvious. This benefit allows the one or more stakeholders to calculate the return on investment of the treatment as it relates to employer resources and incurred costs.

Figure 2:
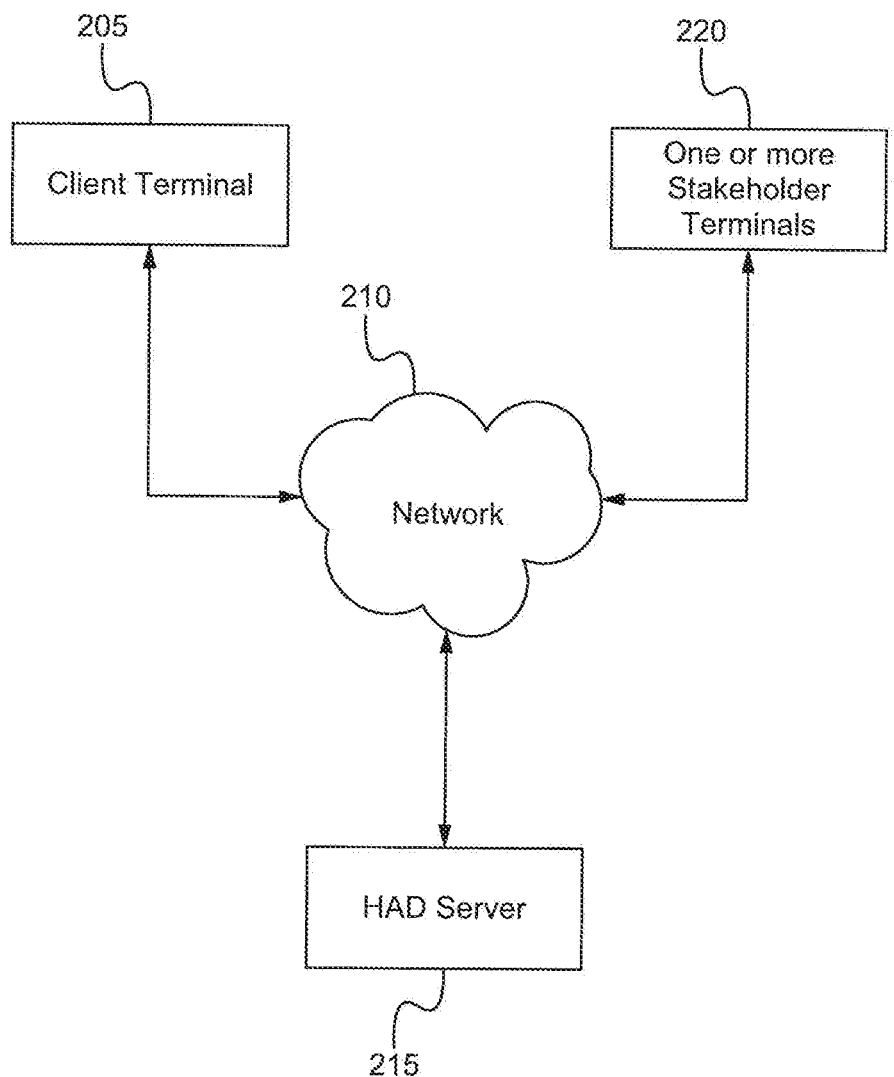
FIG. 2 illustrates a diagram of an exemplary system for optimizing an injury map and treatment actions for a worker's compensation claim across three separate timelines, in accordance with some embodiments.

FIG. 2, illustrates a diagram of an exemplary system 200 in accordance with some embodiments. The system 200 comprises a client terminal 205, a HAD server 215, one or more stakeholder terminals 220 and a network 210, such as the internet. The client terminal 205, the HAD server 215 and the one or more stakeholder terminals 220 are communicatively coupled via the network 210. The HAD 215, such as described above comprises a centralized database of classified body part injuries and/or the injury cohorts. Particularly, in some embodiments, the HAD server 215 comprises real-time injury cohort information that is updated as more injury information is added based on new injuries. The HAD server 215 can comprise real-time injury cohort information that enables one or more stakeholders, such as an injured worker, a treating physician and other stakeholders to compare the injured worker's claim care, delivery of services and costs to similar cohort injuries stored within the HAD 215. For example, in some embodiments, the database comprises one or more ideal or other time value sets for the injury which can be used to calculate one or more delta care values for the individual. Alternatively, the one or more time value sets are further based and/or grouped according to location or age of the injured individual. In some embodiments the HAD 215 comprises a website or web based interface that enables the client terminal 215 and the one or more stakeholder terminals 220 to communicate with the HAD server 215 over the network 210.

The client terminal 205 can be used to input one or more injury inputs, such as described above. As stated above, the one or more injury inputs can comprise an identification of an injured body part, the DOI, DFR, and DOR, pain value, pain frequency and activities of daily living (ADLs) that are impacted. The injury inputs can also comprise actions performed to date or the treatment milestones, such as medication prescriptions and the date of prescription, therapies prescribed and the date, diagnostic tests and the date and any specialty consultations and date, including any surgeries performed and the date. The injury, including the DOI, the DFR and the DOR can then be compared to similar injuries stored within the HAD 215 and based on the DOI, the DFR and the DOR an ideal injury timeline for each of the three treatment modes and analysis can be output. In some embodiments, based on the DOI and the historical data stored within the HAD 215, one or more delta values of treatment can be calculated for the injured individual.

Figure 3:
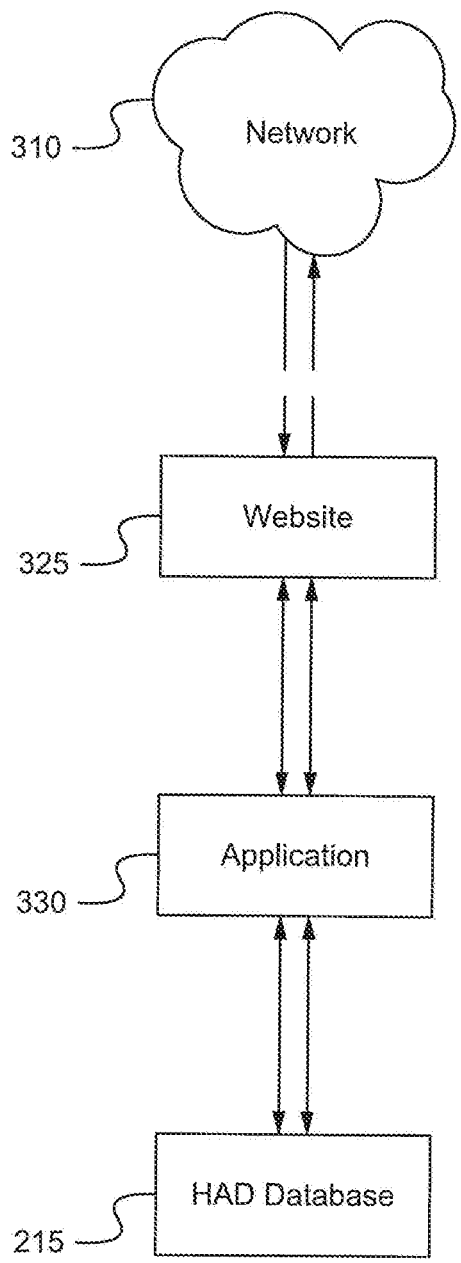
FIG. 3 illustrates a diagram of an exemplary system for optimizing an injury map and treatment actions for a worker's compensation claim across three separate timelines.

FIG. 3 is a diagram illustrating, the system 200, such as described above. The system 300 is utilized to produce an injury map of an injury claim. The system provides a construction of three separate timelines for comparison and analysis including a query to the historical accurate database, such as described above. The system 300 can include one or more software program(s) or application(s) 330 that communicate with the HAD database 215. In some embodiments, the client terminal 205 and the one or more stakeholder terminals 220 communicate with the HAD database 215 through one or more websites 325 and applications 330. The application 330 can implement the steps necessary to communicate with the client terminal 205 and the one or more stakeholder terminals 220. The application 330 can further generate information based on the communications with the client terminal 205 and the one or more stakeholder terminals 220. In some embodiments, the application 330 includes the CRSs used to configure the underlying care delivery expectation times and tolerance of time delivery for the groups of timelines as described above. In some embodiments, the application 330 can communicate with the HAD 215 to categorize an injury and query the HAD 215, to output one or more injury timelines and calculate the one or ore delta values of treatment for the injured individual, such as described above. The HAD includes memory storage of information received from the client terminal 205 and the one or more stakeholder terminals 220 and information generated by the application 330. In some embodiments, the application 330 is stored on the client terminal 205.

Figure 4:
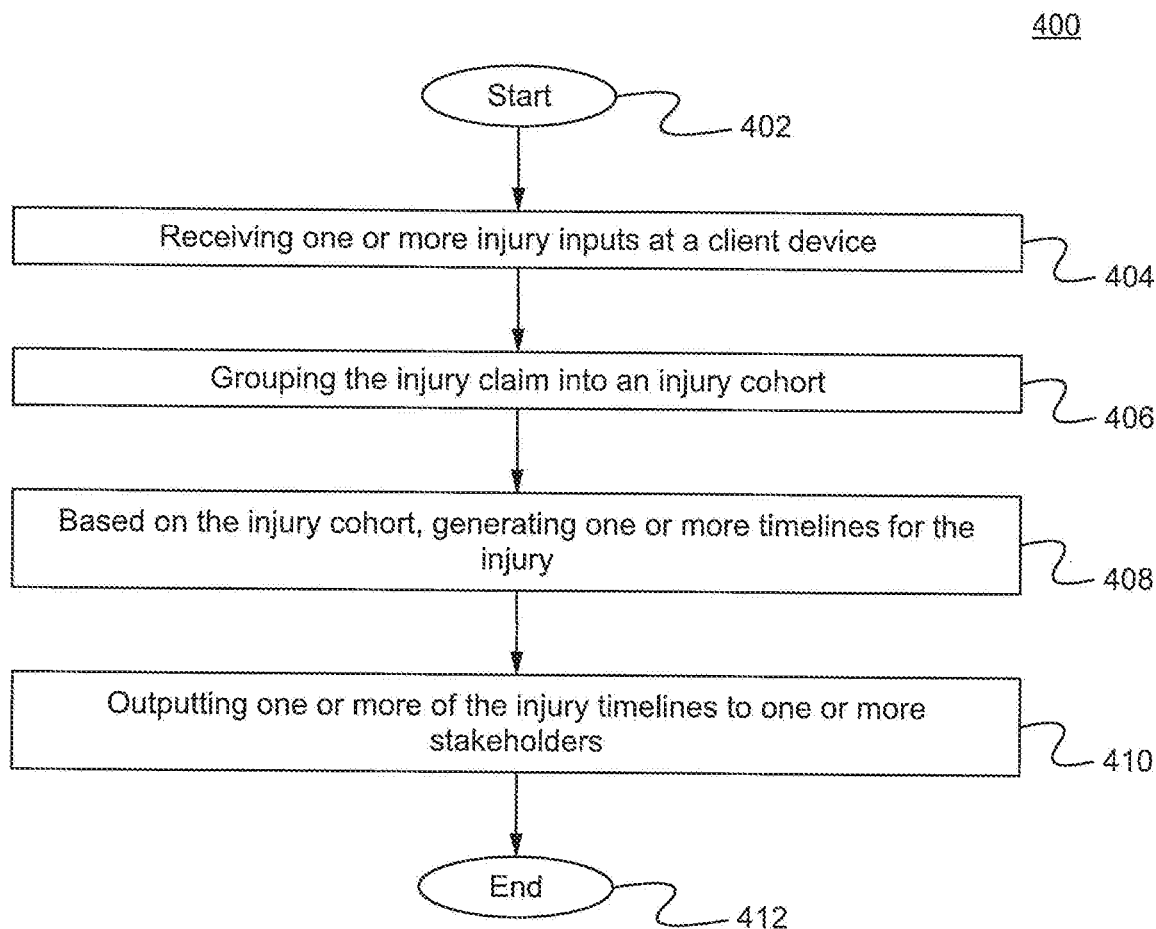
FIG. 4, illustrates a method of producing one or more injury maps for a worker's compensation injury claim.

FIG. 4 illustrates a method of producing one or more injury maps for a worker's compensation injury claim, such as described above. The method begins in the step 402. In the step 404, one or more injury inputs comprising one or more of a worker date of injury, a date of doctor's first report for the injury, and a date of injury review are received at a client device. Then, in the step 406, the injury claim is grouped into an injury cohort. In the step 408, based on the injury cohort, an ideal injury timeline for the worker date of injury, a timeling for the date of doctor's first report and a timeline for the date of injury review are generated and in the step 410, the ideal injury timeline for the worker date of injury, the timeline for the date of doctor's first report and the timeline for the date of injury review are outputted to one or more stakeholder's for the injury.

In some embodiments, each of the timelines comprises an apportionment of injury liability, a whole person impairment rating, a maximum medical improvement date, cost metrics for the injury and injury treatment status. The cost metrics for the injury can comprise one or more of days of delay, medical financial loss and total monetary loss. In some embodiments, the injury treatment status for the injury comprises one or more of completed and pending treatments, treatments behind and on schedule and treatment days delayed. The ideal injury timeline based on the worker date of injury, the timeline based on the date of doctor's first report and the timeline based on the date of injury review are generated according to average historical data for the cohort stored at the HAD server, such as described above. In some embodiments, the historical data for the cohort is updated at the server for each new injury. In some embodiments, the date of doctor's first report and the date of injury review are assigned a delta value based on the date of injury. The ideal injury timeline based on the worker date of injury, the timeline based on the date of doctor's first report and the timeline based on the date of injury review can be compared across a single provider's office, a single medical group, a single claim adjuster, a single insurance company and a single employer. Additionally, the ideal injury timeline based on the worker date of injury, the timeline based on the date of doctor's first report and the timeline based on the date of injury review can be compared across geographic locations. The method ends in the step 412.

The systems and methods such as described above that draws upon actual historical claim data stored within the HAD in conjunction with on demand and available worker's compensation claim pricing allows the creation of a cost/benefit curve analysis. This ability to have claim specific data as a financial output allows the one or more stakeholders to make real-time financial and treatment decisions. Particularly, this provides the one or more stakeholders with the actual monetary value of treatment and also intervention benefit as it relates to the final worker's compensation settlement. The output of the system is reflected in at least two dimensions of the worker's recovery, 1) the injured worker's reports of pain and ADLs and 2) the objective functional measurements, such as range of motion, neurological status and diagnostic findings. Additionally, this impacts the worker's compensation industry by providing greater utilization and review because the system currently depends primarily on patient population cohorts and is not specific to the unique and actual conditions of the individual's injury and recovery response. For example, the MTUs or ODGs, such as described above, may only allow twenty four therapy visits for a shoulder strain. However, the injury map, such as described above indicates that after twelve therapy visits that the cost to settle the claim increases because of worsening pain, ADL reports and/or a decreasing range of motion for the injured worker as compared to the pre-therapy conditions.

In this case, the additional therapy, twelve additional recommended visits is contrary to the calculated injury map. In this case, another mode of therapy such as acupuncture, medical massage or electrical stimulation may be indicated. Similarly, the injury map, such as described above improves and substantiates intervention procedures epidural lumbar injections, where one injection may demonstrate a decreasing trend in settlement price and that may offset the cost of the procedure. For example, the injured worker's settlement cost as determined by the injury map is $45,000 pre-injection and the cost of an injection is $15,000. According to the injury map, six weeks post-operative determines the settlement cost is $20,000 equaling a savings of $25,000. In this case, the injured worker benefits from a faster recovery, data evidenced cost effectiveness and avoiding treatment that is non-beneficial and could potentially be detrimental.

Particularly, as described above, the presently claimed system and method generates a timeline of treatment milestones, determine financial loss and predict MMI of a worker's compensation injury claim. The application of the presently claimed invention includes ARSs used in worker's compensation claims, personal injury claims, social security claims and others. Particularly, the injury map generated, such as described above, is useful to claim stakeholders such as patients, medical providers, insurance carriers, employers and attorneys. The injury map creates timelines from critical treatment milestones to allow a collective understanding and expectation of timely care and also the costs associated with delay, and inefficient system processes within the treatment and care delivery model.

Particularly, to manually duplicate the results afforded by the present invention, a medical practitioner would need to expend thousands and potentially tens of thousands of hours. This makes a non-automatic approach impractical. Moreover, by accumulating the data for all similar injuries into a single database, more accurate results are available than can be generated using conventional current methods Specifically, the presently claimed invention provides a predictive model that instructs the one or more stakeholders when to execute care actions or when the injury requires further evaluation. The invention can also calculate the financial costs of the injury due to delay and waste and determine the date of MMI and the other associated costs. As such, the system and method of determining financial loss for worker's compensation injury claims as described herein has many advantages.

The present invention has been described in terms of specific embodiments incorporating details to facilitate the understanding of the principles of construction and operation of the invention. As such, references, herein, to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A computing system for optimizing an injury map and treatment actions for a worker's compensation claim across three separate timelines, the computing system comprising:
   a shell program executing on a clinician computing device, wherein the shell program controls a graphical user interface on the clinician computing device to guide a clinician user using the clinician computing device through prompts to enter injured worker data for an injured worker according to a plurality of administrative rule sets, and validates the injured worker data as authentic based on the plurality of the administrative rule sets;
   a data repository comprising historical injury information that is updated as new injury information is added based on new injuries; and
   a server coupled with the database and configured to:
      receive the injured worker data from the shell program, the injured worker data including identification of injury, a worker date of injury, a date of doctor's first report, and a date of injury review, wherein each of the worker date of injury, the date of doctor's first report, and the date of injury review are associated with a single worker's compensation claim;
      group the compensation claim in an injury cohort for the injury;
      generate, according at least a portion of the historical injury information that is associated with the injury cohort, a first timeline based on the worker date of injury, a second timeline based on the date of doctor's first report, and a third timeline based on the date of injury review; and
      output the first timeline for the worker date of injury, the second timeline for the date of doctor's first report, and the third timeline for the date of injury review to one or more stakeholder computing devices for display in a web based interface, wherein any two or more timelines selected from the first, second, and third timelines are compared to determine one or more delta values of treatment relating to the injury.

2. The system of claim 1, wherein each of the first, second, and third timelines comprises an apportionment of injury liability, a whole person impairment rating, a maximum medical improvement date, cost metrics for the injury and injury treatment status.

3. The system of claim 2, wherein the injury treatment status for the injury comprises one or more of completed and pending treatments, treatments behind and on schedule and treatment days delayed.

4. The system of claim 2, wherein the cost metrics for the injury comprise one or more of days of delay, medical financial loss and total monetary loss.

5. The system of claim 1, wherein the first timeline based on the worker date of injury, the second timeline based on the date of doctor's first report, and the third timeline based on the date of injury review are generated according to average historical data for the cohort stored at the data repository.

6. The system of claim 5, wherein the historical data for the cohort is updated at the data repository for each new injury.

7. The system of claim 1, wherein the date of doctor's first report and the date of injury review are assigned a delta value based on the date of injury.

8. The system of claim 1, wherein the first timeline based on the worker date of injury, the second timeline based on the date of doctor's first report, and the third timeline based on the date of injury review are comparable across a single provider's office, a single medical group, a single claim adjuster, a single insurance company and a single employer.

9. The system of claim 1, wherein the first timeline based on the worker date of injury, the second timeline based on the date of doctor's first report, and the third timeline on the date of injury review are comparable across geographic locations.

10. A computer-implemented method of producing one or more injury maps for a worker's compensation injury claim, the method comprising:
- executing a shell program on a clinician computing device, wherein the shell program controls a graphical user interface on the clinician computing device to guide a clinician user using the clinician computing device through prompts to enter injured worker data for an injured worker according to a plurality of administrative rule sets, and validates the injured worker data as authentic based on the plurality of the administrative rule sets;
- storing, in a database, historical injury cohort information that is updated as new injury information is added based on new injuries;
- receiving, at a server coupled with the database, the injured worker data from the shell program, the injured worker data including identification of injury, a worker date of injury, a date of doctor's first report for the injury, and a date of injury review, wherein each of the worker date of injury, the date of doctor's first report, and the date of injury review are associated with a single worker's injury claim;
- grouping the injury claim into an injury cohort for the injury;
- generating, by the server, according to at least a portion of the historical injury information that is associated with the injury cohort, a first timeline for the worker date of injury, a second timeline for the date of doctor's first report, and a third timeline for the date of injury review; and
- outputting, by the server, the first timeline for the worker date of injury, the second timeline for the date of doctor's first report, and the third timeline for the date of injury review to one or more stakeholder computing devices for display in a web based interface, wherein any two or more timelines selected from the first, second, and third timelines are compared to determine one or more delta values of treatment relating to the injury.

11. The method of claim 10, wherein each of the first, second, and third timelines comprises an apportionment of injury liability, a whole person impairment rating, a maximum medical improvement date, cost metrics for the injury and injury treatment status.

12. The method of claim 11, wherein the injury treatment status for the injury comprises one or more of completed and pending treatments, treatments behind and on schedule and treatment days delayed.

13. The method of claim 11, wherein the cost metrics for the injury comprise one or more of days of delay, medical financial loss and total monetary loss.

14. The method of claim 10, wherein the first timeline based on the worker date of injury, the second timeline based on the date of doctor's first report, and the third timeline based on the date of injury review are generated according to average historical data for the cohort stored at the data repository.

15. The method of claim 14, wherein the historical data for the cohort is updated at the data repository for each new injury.

16. The method of claim 10, wherein the date of doctor's first report and the date of injury review are assigned a delta value based on the date of injury.

17. The method of claim 10, wherein the first timeline based on the worker date of injury, the second timeline based on the date of doctor's first report, and the third timeline based on the date of injury review are comparable across a single provider's office, a single medical group, a single claim adjuster, a single insurance company and a single employer.

18. The method of claim 10, wherein the first timeline based on the worker date of injury, the second timeline based on the date of doctor's first report, and the third timeline on the date of injury review are comparable across geographic locations.

19. The system of claim 1, wherein the server is further configured to generate, from at least the portion of the cohort information that is associated with the injury cohort, the injury map nexus that includes a treatment action and a date of action to achieve maximum medical improvement (MMI).

* * * * *